United States Patent
Amineh et al.

(10) Patent No.: US 10,539,534 B2
(45) Date of Patent: Jan. 21, 2020

(54) DETECTION OF PIPE CHARACTERISTICS WITH A REMOTE FIELD EDDY CURRENT

(71) Applicant: Halliburton Energy Services, Inc., Houston, TX (US)

(72) Inventors: Reza Khalaj Amineh, Houston, TX (US); Luis Emilio San Martin, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/580,131

(22) PCT Filed: Nov. 6, 2016

(86) PCT No.: PCT/US2016/060750
§ 371 (c)(1),
(2) Date: Dec. 6, 2017

(87) PCT Pub. No.: WO2018/084862
PCT Pub. Date: May 11, 2018

(65) Prior Publication Data
US 2019/0056355 A1 Feb. 21, 2019

(51) Int. Cl.
*G01R 31/00* (2006.01)
*G01N 27/90* (2006.01)
(Continued)

(52) U.S. Cl.
CPC .......... *G01N 27/902* (2013.01); *E21B 12/02* (2013.01); *E21B 47/00* (2013.01); *E21B 47/124* (2013.01)

(58) Field of Classification Search
USPC ................. 324/338–343, 635, 716
See application file for complete search history.

(56) References Cited

U.S. PATENT DOCUMENTS

| 7,960,969 B2 | 6/2011 | Mouget et al. |
| 9,512,712 B2 | 12/2016 | Donderici et al. |

(Continued)

FOREIGN PATENT DOCUMENTS

| EP | 0816838 | 1/1998 |
| EP | 2270420 | 1/2011 |
| WO | 2016007305 | 1/2016 |

OTHER PUBLICATIONS

International Search Report and Written Opinion for Application No. PCT/US2016/060750 dated Jul. 13, 2017.

(Continued)

*Primary Examiner* — Vincent Q Nguyen
(74) *Attorney, Agent, or Firm* — Benjamin Fite; C. Tumey Law Group PLLC

(57) ABSTRACT

Methods for detection of pipe characteristics, such as defect detection of downhole tubulars and overall thickness estimation of downhole tubulars, utilizing remote-field eddy current technique. A defect detection method may further include disposing a defect detection tool in a wellbore, wherein the defect detection tool comprises a transmitter and a plurality of receivers, recording measurements for a plurality of channels, utilizing pre-calculated estimation curves corresponding to the plurality of channels at a plurality of defected candidates to obtain thicknesses corresponding to the plurality of channels at each defected candidate; and evaluating variations for the thicknesses by computing standard deviations between the thicknesses obtained for the plurality of channels at each defected candidates utilizing a minimum variation, and computing an overall thickness change using overall thickness estimations for the plurality of defected candidates.

20 Claims, 6 Drawing Sheets

(51) Int. Cl.
*E21B 47/00* (2012.01)
*E21B 12/02* (2006.01)
*E21B 47/12* (2012.01)

(56) References Cited

U.S. PATENT DOCUMENTS

| | | |
|---|---|---|
| 9,513,398 B2 | 12/2016 | Wilson et al. |
| 9,562,877 B2 | 2/2017 | Amineh et al. |
| 9,562,988 B2 | 2/2017 | Wilson et al. |
| 9,664,028 B2 | 5/2017 | Donderici et al. |
| 9,690,004 B2 | 6/2017 | Donderici et al. |
| 9,696,451 B2 | 6/2017 | Lie et al. |
| 9,726,781 B2 | 8/2017 | San Martin et al. |
| 9,745,845 B2 | 8/2017 | San Martin et al. |
| 2009/0195244 A1 | 8/2009 | Mouget et al. |
| 2010/0017137 A1 | 1/2010 | Legendre et al. |
| 2013/0193953 A1 | 8/2013 | Yarbro et al. |
| 2015/0127274 A1 | 5/2015 | Legendre et al. |
| 2015/0241211 A1* | 8/2015 | Pehle ............... B21B 38/04 702/35 |
| 2016/0069842 A1 | 3/2016 | Bonavides et al. |
| 2016/0168975 A1 | 6/2016 | Donderici et al. |
| 2016/0290966 A1* | 10/2016 | Koenig ............... G01N 27/9053 |
| 2017/0068016 A1 | 3/2017 | Donderici et al. |
| 2018/0074220 A1* | 3/2018 | David ............... G01V 3/38 |

OTHER PUBLICATIONS

"Fundamental analysis of the remote-field eddy-current effect", by S.M. Haugland, published in IEEE Transaction on Magnetics vol. 32, No. 4, pp. 3195-3211, in 1996.

Search report French application No. 1759338, dated Jul. 5, 2019.

* cited by examiner

DETECTION OF PIPE CHARACTERISTICS WITH A REMOTE FIELD EDDY CURRENT

BACKGROUND

For oil and gas exploration and production, a network of wells, installations and other conduits may be established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, and corrosion transfer, among others. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data may be interpreted to correlate a level of flux leakage or EM induction with corrosion. When multiple casing strings are employed together, correctly managing corrosion detection EM logging tool operations and data interpretation may be complex.

BRIEF DESCRIPTION OF THE DRAWINGS

These drawings illustrate certain aspects of some examples of the present disclosure, and should not be used to limit or define the disclosure.

DETAILED DESCRIPTION

Figure 1:
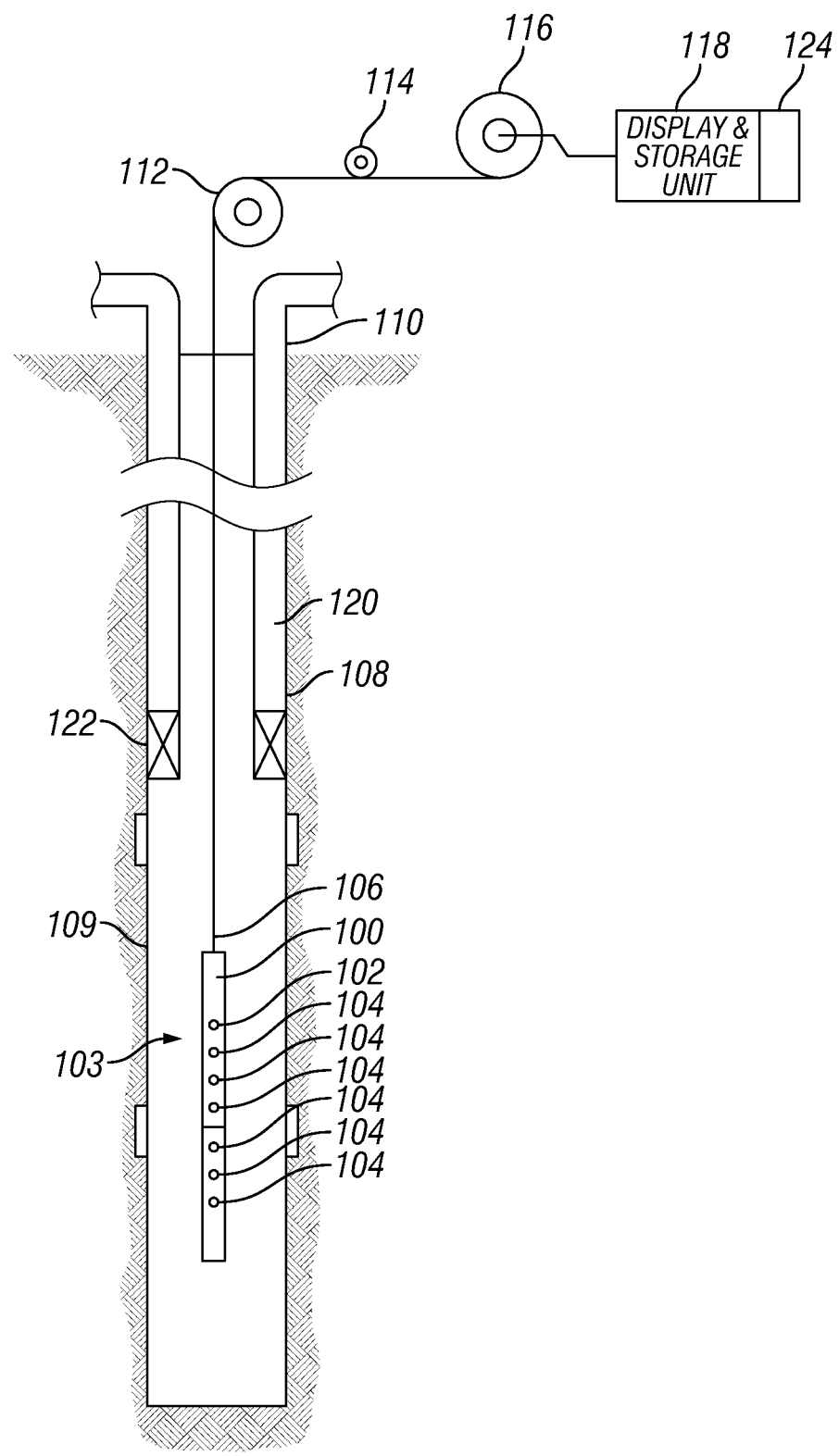
FIG. 1 is a schematic illustration of an operating environment for a defect detection tool.

This disclosure may generally relate to methods for detection of pipe characteristics, such as defect detection of downhole tubulars and overall thickness estimation of downhole tubulars, utilizing remote-field eddy current ("RFEC") technique.

The disclosed approaches may have the following advantages: (i) in addition to the overall thickness estimation for multiple pipes, the disclosed approaches may detect which pipe(s) is (are) defected; (ii) By combining the results from multiple receivers and multiple frequencies, the evaluation process may be more robust to noise; (iii) This approach may still be substantially faster than the standard optimization-based inversion approaches in which the forward model needs to be evaluated many times; (iv) Characterization of the multiple pipes with better resolution and accuracy (for thickness estimation) may provide a more precise evaluation of these components and ultimately lead to a significant positive impact on the production process.

Monitoring the condition of the production tubing and possibly multiple casing strings may be desirable in oil and gas field operations. Electromagnetic ("EM") techniques may be common in inspection of these components. EM techniques may include two broad categories: (1) techniques based on the magnetic flux leakage ("MFL") and (2) techniques based on eddy current ("EC"). While MFL techniques may be more suitable for single pipe inspections, EC techniques may allow for the multiple pipes characterizations. EC techniques themselves may be divided into two categories, frequency-domain EC techniques and time-domain EC techniques.

In frequency-domain EC techniques, a transmitter (e.g., coil) may be fed by a continuous sinusoidal signal, producing primary fields that may illuminate the pipes. The primary fields may produce eddy currents in the pipes. These eddy currents, in turn, may produce secondary fields that may be sensed along with the primary fields in the receiver coils that may be placed at a distance from the transmitter. Characterization of the pipes may be performed by measuring and processing these fields.

In time-domain EC techniques (also referred to as pulsed EC (PEC)), the transmitter may be fed by a pulse. Similar to the frequency-domain technique, transient primary fields may be produced due to the transition of the pulse from "off" to "on" state or from "on" to "off" state (more common). These transient fields may produce eddy currents in the pipes. The eddy currents may then produce secondary magnetic fields that may be measured by either a separate receiver coil placed further away from the transmitter, a separate coil co-located with the transmitter, or the same coil that was used as the transmitter.

In frequency domain EC, as mentioned above, the frequency of the excitation may be adjusted so that multiple reflections in the wall of the pipe are insignificant and the spacing between the coils may be large enough that the contribution to the mutual impedance from the dominant (but evanescent) waveguide mode may be small compared to the contribution to the mutual impedance from the branch cut component, the RFEC effect may be observed. In a RFEC regime, the mutual impedance between the transmitter and the receiver (e.g., coil), may be very sensitive to the thickness of the pipe wall. To be more specific, the phase of the impedance may vary as $$\varphi = 2\sqrt{\frac{\omega\mu\sigma}{2}}t \quad (1)$$

and the magnitude of the impedance shows the dependence:

$$\exp[-2(\sqrt{\omega\mu\sigma/2})t] \quad (2)$$

where ω is the angular frequency of the excitation source, μ is the magnetic permeability of the pipe, σ is the electrical conductivity of the pipe, and t is the thickness of the pipe. By using the common definition of skin depth for the metals as:

$$\delta = \sqrt{\frac{2}{\omega\mu\sigma}} \quad (3)$$

The phase of the impedance may vary as:

$$\varphi \approx 2\frac{t}{\delta} \quad (4)$$

and the magnitude of the impedance shows the dependence:

$$\exp[-2t/\delta] \quad (5)$$

In RFEC, the estimated quantity may be the overall thickness of the metal. Thus, for multiple pipes, the estimated parameter may be the overall or sum of the thicknesses of the pipes.

FIG. 1 illustrates an operating environment for a defect detection tool 10 as disclosed herein. Defect detection tool 100 may comprise transmitter 102 (e.g., coil) receivers 104 (e.g., coil). Defect detection tool 100 may be operatively coupled to conveyance line 106 (e.g., wireline or slickline) which may provide electrical connectivity, as well as mechanical suspension, for defect detection tool 100. Conveyance line 106 and defect detection tool 100 may extend within casing string 108 to a desired depth within the wellbore 109. Conveyance line 106, which may include one or more electrical conductors, may exit wellhead 110, may pass around pulley 112, may engage odometer 114, and may be reeled onto winch 116, which may be employed to raise and lower the tool assembly in the wellbore 109. The electrical signals from conveyance line 106 may be conducted from winch 116 to display and storage unit 118 where the signals may be processed, and the information contained therein may be displayed for an operator to observe and stored for future processing and reference. Display and storage unit 118 may also contain an apparatus for supplying control signals and power to the downhole tool assembly, wherein the downhole tool assembly may comprise defect detection tool 100.

A typical casing string 108 may extend from wellhead 110 at or above ground level to a selected depth within a wellbore 109. Casing string 108 may comprise a plurality of joints or segments of casing, each segment being connected to the adjacent segments by a threaded collar.

FIG. 1 also illustrates a typical tubing string 120, which may be positioned inside of casing string 108 extending part of the distance down wellbore 109. A packer 122 typically may seal the lower end of the tubing-casing annulus and may secure the lower end of the tubing string 120 to the casing. The defect detection tool 100 may be dimensioned so that it may be lowered into the wellbore 109 through the tubing, thus avoiding the difficulty and expense associated with pulling the tubing out of the wellbore 109.

In logging systems, such as, for example, logging systems utilizing the defect detection tool 100, a digital telemetry system may be employed, wherein an electrical circuit is used to both supply power to the defect detection tool 100 and to transfer data between display and storage unit 118 and defect detection tool 100. A DC voltage may be provided to the defect detection tool 100 by a power supply located above ground level, and data may be coupled to the DC power conductor by a baseband current pulse system. Alternatively, the defect detection tool 100 may be powered by batteries located within the downhole tool assembly, and/or the data provided by the defect detection tool 100 may be stored within the downhole tool assembly, rather than transmitted to the surface during logging (defect detection).

Transmission of electromagnetic fields by the transmitter 102 and the recordation of signals by the receivers 104 may be controlled by an information handling system. Transmitter 102 and receivers 104 may include coils.

Systems and methods of the present disclosure may be implemented, at least in part, with an information handling system 124. An information handling system 124 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 124 may be a personal computer, a network storage device, or any other suitable device and may vary in size, shape, performance, functionality, and price. The information handling system 124 may include random access memory (RAM), one or more processing resources such as a central processing unit (CPU) or hardware or software control logic, ROM, and/or other types of nonvolatile memory. Additional components of the information handling system 124 may include one or more disk drives, one or more network ports for communication with external devices as well as various input and output (I/O) devices, such as a keyboard, a mouse, and a video display. The information handling system 124 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 2:
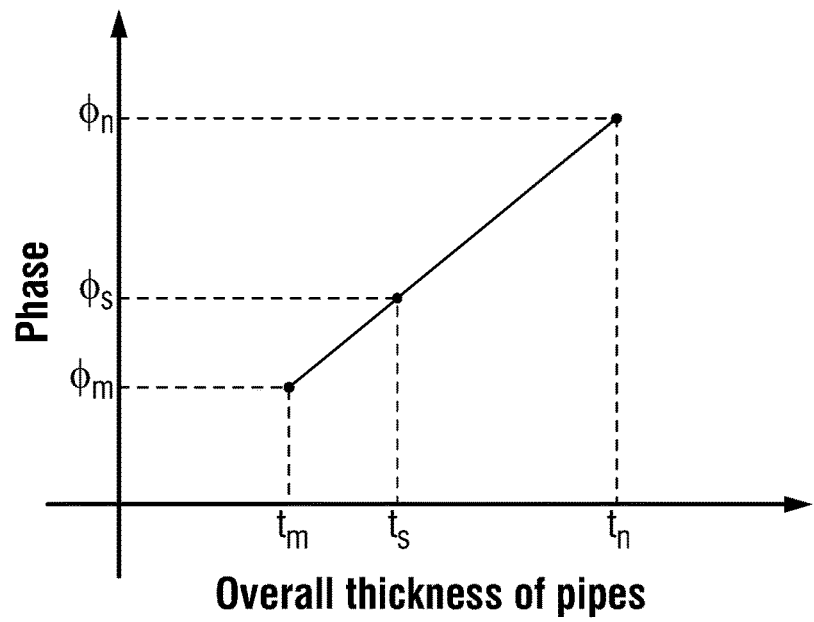
FIG. 2 is a schematic illustration of phase of mutual impedance between the transmitter and the receiver vs. an overall thickness of pipes.

Defection detection tool 100 may be used for excitation of transmitters 102. Transmitters 102 may transmit electromagnetic signals into a subterranean formation. The electromagnetic signals may be received and measured by receivers 104 and processed by information handling system 124 to determine pipe parameters, such as, for example, pipe thickness and defected pipes. The quasi-linear variation of the phase of mutual impedance with the overall metal thickness may be employed to perform fast inversion to estimate the overall thickness of multiple pipes. For this purpose, for any given set of pipes dimensions, material properties, and tool configuration, such linear variation may be constructed quickly and be used to estimate the overall thickness of the pipes quickly. To establish this linear variation, two simulations may be performed. One simulation with the nominal section of the pipes (overall thickness $t_n$) and a second simulation with an overall thickness change for the pipes such that this overall thickness change ($\Delta t = t_n - t_m$) may be larger than any possible overall thickness change for the test configurations. By having the simulated phases $\varphi_n$ and $\varphi_m$ corresponding to overall thicknesses of $t_n$ and $t_m$, a line may be established as shown in FIG. 2 between the points ($t_n, \varphi_n$) and ($t_m, \varphi_m$). This line may be employed for the inversion of any other measured phase to the overall thickness of the pipes for any unknown defected section. For example, FIG. 2 shows that a measured phase of the defected section $\varphi_s$ can be inverted to the overall thickness $t_s$ when using this linear approximation. FIG. 2 illustrates establishing the estimation line required for the inversion based on the RFEC assumptions between two points $(t_n, \varphi_n)$ and $(t_m, \varphi_m)$ corresponding to maximum (nominal) and minimum possible overall thicknesses of the pipes. Any unknown overall thickness $t_s$ may then be estimated from this line given the measured phase at the defected section $\varphi_s$.

A practical method for the inversion may be to use the differential phase instead of the absolute phase to construct the estimation line described above. In this approach, the differential phase may be the difference in the phase measured at the nominal section (non-defected section) of the pipes and the defected section.

Figure 3:
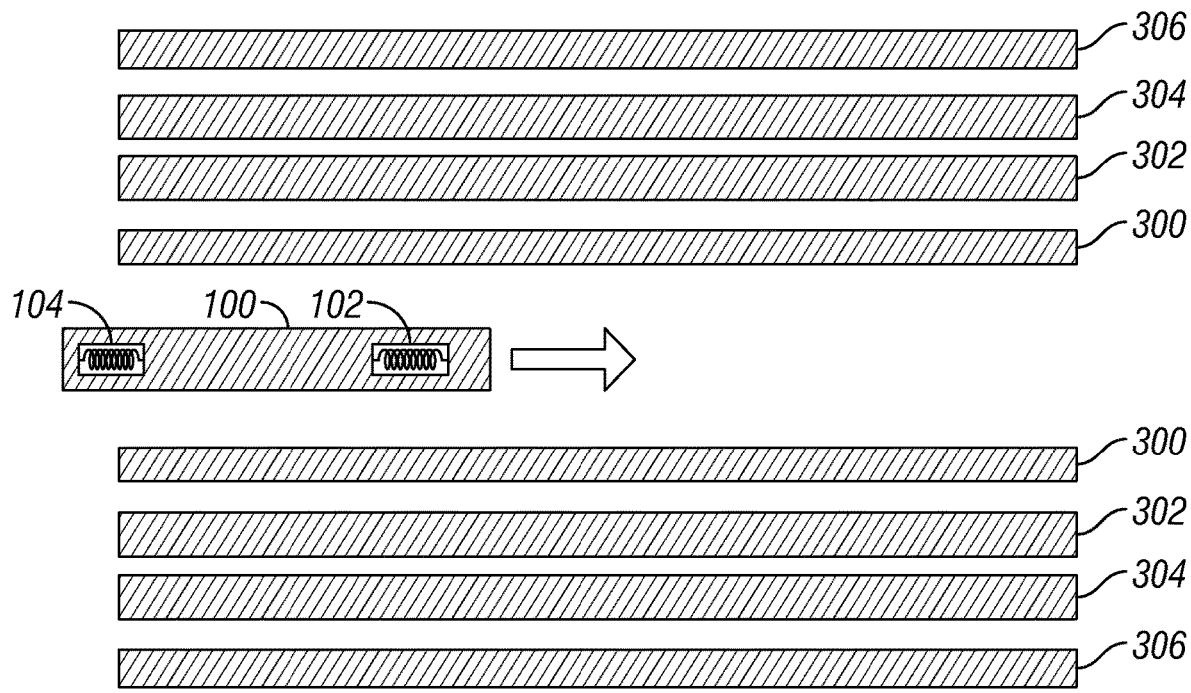
FIG. 3 is a schematic illustration of a configuration of a defect detection tool comprising a transmitter and receiver that may be used for logging four concentric pipes.
Figure 4:
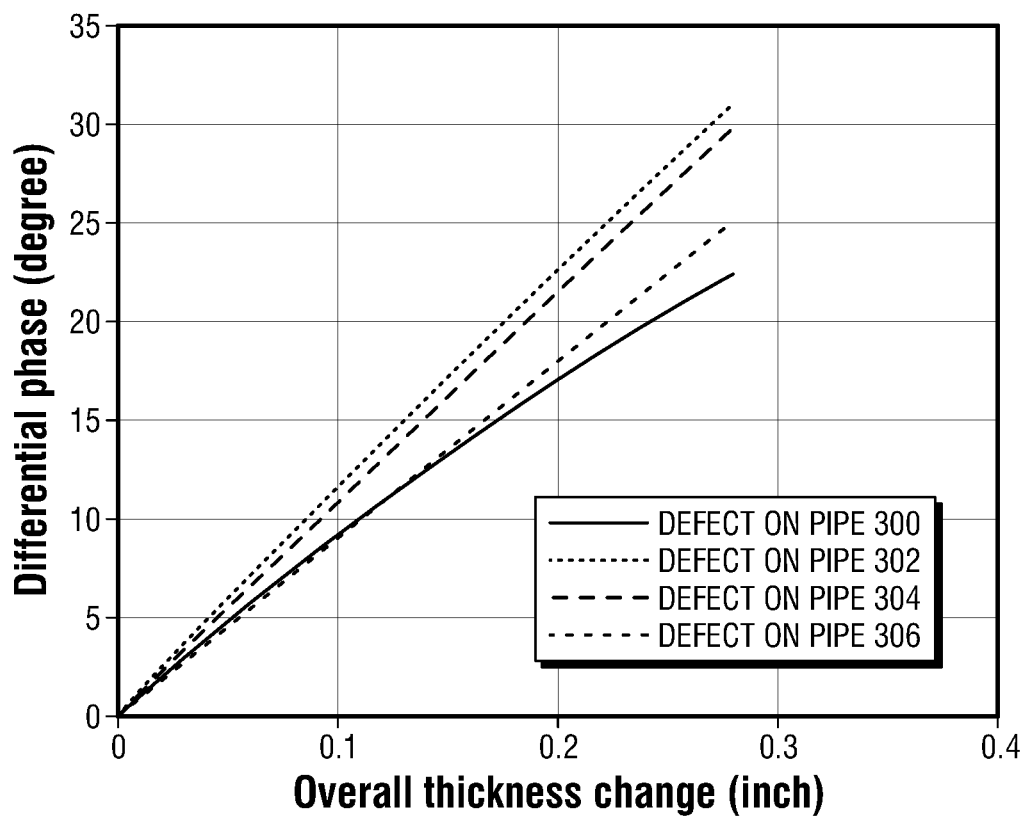
FIG. 4 is a schematic illustration of a simulated differential phase versus the overall thickness change of pipes.

As described above, conventionally, in RFEC techniques, the estimated quantity may be the overall thickness of multiple pipes. In conventional RFEC pipe inspection, it may be assumed that the same amount of thickness change on various pipes may produce the same amount of phase shift for the mutual impedance. However, in reality there would be a slight difference between the phase shifts obtained due to the same thickness changes on various pipes. For example, FIG. 3 illustrates the configuration of a defect detection tool 100 comprising transmitter 102 and receiver 104 that may be used for logging four concentric pipes: pipe 300 which may be positioned in pipe 302 which may be positioned in pipe 304 which may be positioned in pipe 306. Without limitation, the number of turns for the coils of transmitter 102 and receiver 104 may vary from about 100 to about 50,000 turns. Without limitation, the length of the coils may vary from about 1 inch to about 20 inches. Without limitation, the spacing between the transmitter 102 and the receiver 104 may vary from about 5 inches to about 80 inches. Table 1 shows the parameters of the pipes 300, 302, 304 and 306. FIG. 4 illustrates the simulated differential phase versus the overall thickness change of the pipes 300, 302, 304 and 306 when each time one of the pipes 300, 302, 304 and 306 is defected, i.e. each time the thickness of one of the pipes 300, 302, 304 and 306 is changing. Such difference in the responses of the four plots can be exploited for detection of the defected pipe using RFEC-based inversion. It may be observed from FIG. 3 that the variation of the differential phase versus overall thickness change may show differences when the defect is on the different pipes. Thus, such differences may be employed to distinguish the defected pipe(s).

TABLE 1

Dimensions of the pipes 300, 302, 304 and 306.

|  | Pipe 300 | Pipe 302 | Pipe 304 | Pipe 306 |
|---|---|---|---|---|
| OD (inches) | 5 | 9 + 5/8 | 13 + 3/8 | 18 + 5/8 |
| Nominal thickness (inches) | 0.4 | 0.4 | 0.4 | 0.4 |

Detection of a Single Defected Pipe.

The following describes an example technique to detect the defected pipe (in addition to the estimation of the overall thickness of the pipes) in a multiple pipe inspection process (pipes 1 to $N_p$) with RFEC-based inversion.

In a multiple pipe configuration (pipes 1 to $N_p$), the k-th pipe may be defected. In order to detect this defected pipe, $N_p$ separate RFEC estimation lines, $L_1$ to $L_{Np}$ may be constructed similar to the one shown in FIG. 2, every time assuming that the defect is on one of the pipes 1 to $N_p$. Then, for any tested configuration, these estimation lines may be employed to invert the measured differential phase to the overall thickness of the pipes 300, 302, 304 and 306 (shown in FIG. 3). This may provide the overall thickness estimations $T_1$ to $T_{Np}$ that may be slightly different from each other due to the slight differences in the estimation lines $L_1$ to $L_{Np}$. If using a single receiver (e.g., receiver 104 shown on FIG. 3) and the measurement at a single frequency, it may not be possible to distinguish the defected pipe and use the corresponding estimation line to obtain the most accurate estimation of the overall thickness of the pipes 300, 302, 304 and 306. However, measurements with multiple receivers (e.g., at least two receivers 104 shown on FIG. 1) $RX_1$ to $RX_{Nr}$ and/or at multiple frequencies $f_1$ to $f_{Nf}$ (e.g., at least two frequencies), and for the measurement of each receiver $RX_i$ at each frequency $f_j$ that may be referred to as "channels," the corresponding estimation lines $L_1^{i,j}$ to $L_{Np}^{i,j}$ (for producing them, each time it may be assumed that the defect may be on one of the pipes 300, 302, 304 and 306) may be used to provide the overall thickness estimations $T_1^{i,j}$ to $T_{Np}^{i,j}$. Thus, the number of overall thickness estimations are $N_p$. To detect the defected pipe, it may be assumed if, for example, pipe k is defected, the overall thickness estimations $T_k^{i,j}$ for i=1, . . . , $N_r$, and j=1, . . . , $N_f$ have the least variations (are the most consistent results) while the other overall thickness estimations based on the assumption that any other pipe k' is defected ($T_{k'}^{i,j}$ for i=1, . . . , $N_r$, and j=1, . . . , $N_f$) may have more variation and inconsistency. Thus, when comparing the consistency of the results with a suitable parameter such as standard deviation, when pipe k is defected, the lowest standard deviation may be obtained for $T_1^{i,j}$ (for i=1, . . . , $N_r$, and j=1, . . . , $N_f$) estimations while for any other assumption, $T_{k'}^{i,j}$ (for i=1, . . . , $N_r$, j=1, . . . , $N_f$, and k'≠k) the standard deviations may be larger. This may lead to the detection of pipe k as the defected pipe and the average or weighted average of $T_k^{i,j}$, for i=, . . . , $N_r$, and j=1, . . . , $N_f$, as the most accurate overall thickness estimation result. The two smallest standard deviations may be utilized as a quality factor.

Figure 5:
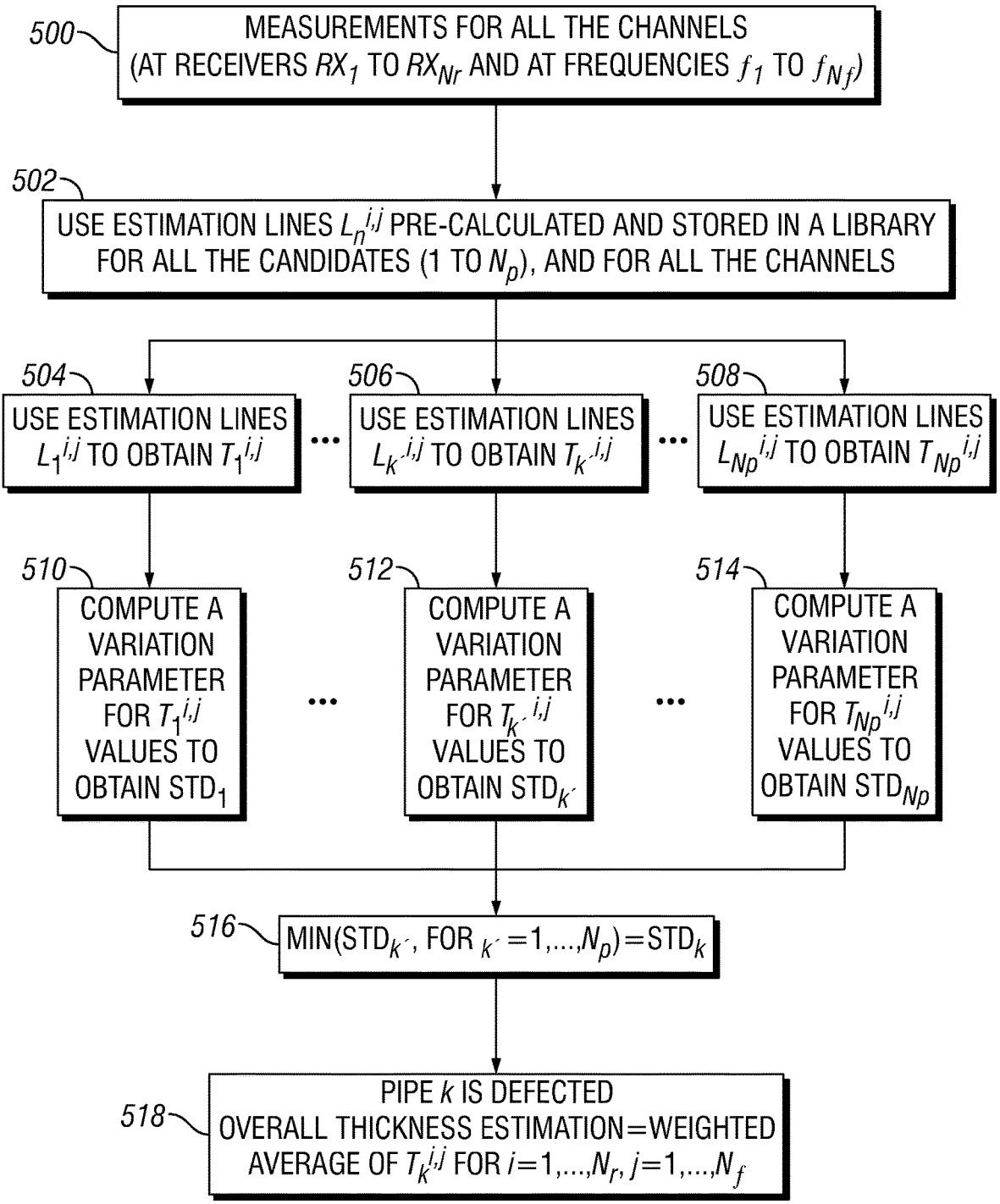
FIG. 5 is a schematic illustration of a flow chart summarizing the steps for detecting a single defected pipe.
Figure 6:
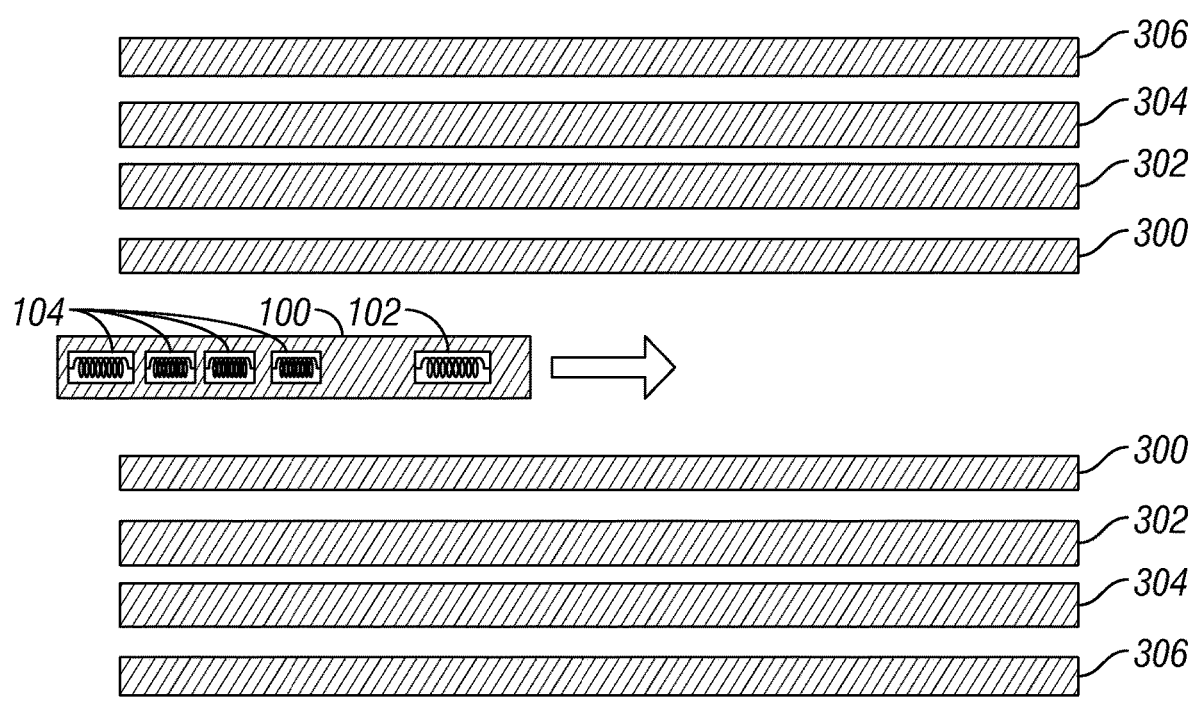
FIG. 6 is a schematic illustration of a defect detection tool with multiple receivers for evaluating multiple pipes.

FIG. 5 summarizes the steps disclosed above. Box 500 may provide measurements for all the channels (at receivers $RX_1$ to $RX_{Nr}$ at frequencies $f_1$ to $f_{Nf}$). Box 502 may use estimation lines $L_n^{i,j}$ pre-calculated and stored in a library for all the candidates (1 to $N_p$), and for all the channels. Each candidate may include a tubular (e.g., pipe) being analyzed. Box 504 may use the estimation lines $L_1^{i,j}$ to obtain $T_1^{i,j}$. Box 506 may provide estimation lines $L_k^{i,j}$ to obtain $T_k^{i,j}$. Box 508 may provide estimation lines $L_{np}^{i,j}$ to obtain $T_{np}^{i,j}$. Box 510 may compute a variation parameter for $T_1^{i,j}$ values to obtain $STD_1$. Box 512 may compute a variation parameter for $T_k^{i,j}$ values to obtain $STD_k$. Box 514 may compute a variation parameter for $T_{np}^{i,j}$ values to obtain $STD_{np}$. Box 516 may provide $Min(STD_{k'}$, for k'=1, . . . , $N_p$)=$STD_k$. Box 518 may provide that pipe set k is defected. Overall thickness estimation=weighted average of $T_k^{i,j}$ for i=1, . . . , $N_r$, j=1, . . . , $N_f$.

Detection of Multiple Defected Pipes.

As an extension of the previous description directed to an example technique for detection of a single defected pipe, an example technique to detect multiple defected pipes (in addition to the estimation of the overall thickness of the pipes) in a multiple pipe inspection process (pipes 1 to $N_p$) with RFEC-based inversion will now be described. It may be assumed that in a multiple pipe configuration (pipes 1 to $N_p$), $N_d$ pipes are defected. In order to detect these defected pipes, several RFEC estimation lines with the number of estimation lines M being equal to the $N_d$ combination of $N_p$ pipes may be constructed, every time assuming that the defect is on a different set of $N_d$ pipes out of $N_p$ pipes. In the mathematical terms, the relation between M, $N_d$, and $N_p$ may be written as:

$$M = N_t^{N_d} \binom{N_p}{N_d} \qquad (6)$$

In other words, a possibility of M set of defected pipes that in each set m (m=1, ..., M), $N_d$ pipes out of $N_p$ pipes may be defected with one of the $N_t^{N_d}$ thickness change distributions among the $N_d$ pipes when constructing the corresponding estimations lines, may be considered.

Then, for any tested configuration, these estimation lines may be employed to invert the measured differential phase to the overall thickness of the pipes 300, 302, 304 and 306 (shown in FIG. 3). This may provide overall thickness estimations $T_1$ to $T_M$ that may be slightly different from each other due to the slight differences in the estimation lines $L_1$ to $L_M$. If using a single receiver 104 (shown in FIG. 3) and the measurement at a single frequency, it may not be possible to distinguish the defected pipe and use the corresponding estimation line to obtain the most accurate estimation of the overall thickness of the pipes 300, 302, 304 and 306. However, measurements with multiple receivers $RX_1$ to $RX_{Nr}$ and/or at multiple frequencies $f_1$ to $f_{Nf}$, and for the measurement of each receiver $RX_i$ at each frequency $f_j$ that may be referred to as "channel" may be used. Corresponding estimation lines $L_1^{i,j}$ to $L_M^{i,j}$ (for producing them, each time it may be assumed that the defect is on $N_d$ pipes out of $N_p$ pipes with thickness change distribution profile one out of $N_t^{N_d}$ cases) may be used to provide the overall thickness estimations $T_1^{i,j}$ to $T_M^{i,j}$. Thus, the number of overall thickness estimations are $N_r N_f M$. To detect the defected pipes, for example, it may be assumed that the m-th set of pipes are actually defected (m can be any number between 1 to MA), the overall thickness estimations $T_m^{i,j}$ for i=1, ..., $N_r$ and j=1, ..., $N_f$ have the least variations (are the most consistent results) while the other overall thickness estimations based on the assumption that any other set of pipes m' is defected ($T_{m'}^{i,j}$ for i=1, ..., $N_r$ and j=1, ..., $N_f$) have more variations. Thus, when comparing the variation of the results with a suitable parameter such as standard deviation, when pipe set m is defected, the lowest standard deviation may be obtained for $T_m^{i,j}$ (for i=1, ..., $N_r$ and j=1, ..., $N_f$) estimations while for any other assumption, $T_{m'}^{i,j}$ (for i=1, ..., $N_r$, j=1, ..., $N_f$ and m'≠m) the standard deviations may be larger. This may leads to the detection of pipe set in as the defected pipes and the average or weighted average of $T_m^{i,j}$, for i=1, ..., $N_r$ and j=1, ..., $N_f$, as the most accurate overall thickness estimation result.

A General Approach in Detection of Multiple Defected Pipes.

Disclosed above may be approaches to detect single or multiple defected pipes assuming looking for a certain number of defected pipes (number of defected pipes was assumed to be known).

A more general technique in which the number of the defected pipes can be unknown is described below. In this example technique, the number of defected pipes may be estimated in addition to the detection of the defected pipes themselves and an accurate estimation of the overall thickness of the pipes may be provided.

It may be assumed that in a multiple pipe configuration (pipes 1 to $N_p$), the number and that which pipes are defected are unknown. To solve this problem, several RFEC estimation lines with the number of estimation lines M being equal to the sum of n-combination of $N_p$ pipes for n from 1 to $N_p$, times $N_t^n$ where $N_t$ is the number of thickness change levels assumed for each defected pipe may be constructed. In the mathematical terms, the relation between M, n, and $N_p$ may be written as:

$$M = N_t^{\square}\binom{N_p}{1} + \ldots + N_t^n\binom{N_p}{n} + \ldots + N_t^{N_p}\binom{N_p}{N_p} \qquad (7)$$

In other words, there may be a possibility of M set of defected pipes that in each set m (m=1, ..., M), n (n=1, ..., $N_p$) pipes out of $N_p$ pipes are defected with one of the $N_t^n$ thickness change distributions among the n pipes when constructing the corresponding estimations lines.

Figure 7:
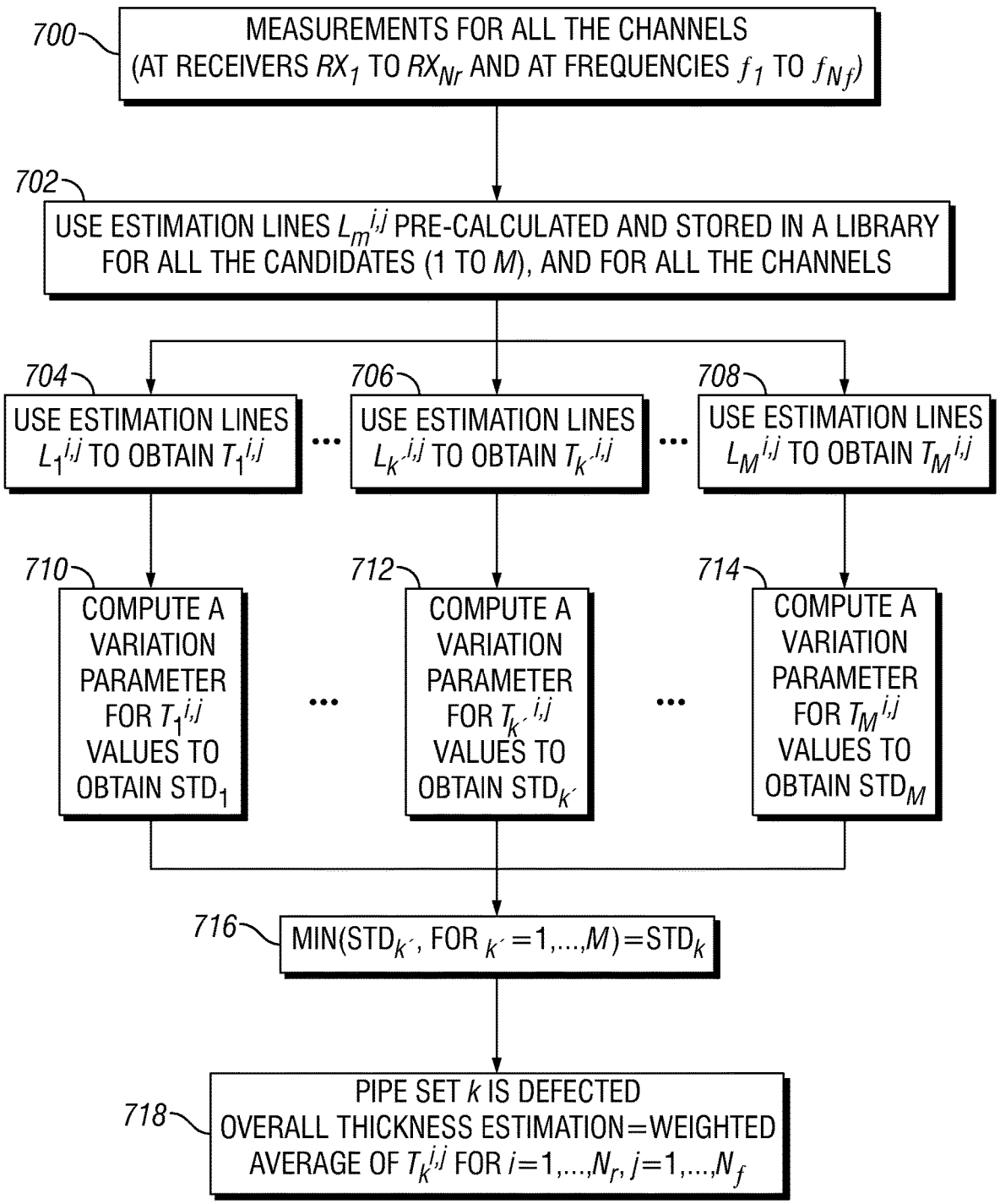
FIG. 7 is a schematic illustration of a flow chart summarizing the steps for detecting multiple defected pipes.

FIG. 7 summarizes the steps disclosed above. Box 700 may provide measurements for all the channels (at receivers $RX_1$ to $RX_{Nr}$ at frequencies $f_1$ to $f_{Nf}$). Box 702 may use estimation lines $L_m^{i,j}$ pre-calculated and stored in a library for all the candidates (1 to M), and for all the channels. Box 704 may use the estimation lines $L_1^{i,j}$ to obtain $T_1^{i,j}$. Box 706 may provide estimation lines $L_k^{i,j}$ to obtain $T_k^{i,j}$. Box 708 may provide estimation lines $L_m^{i,j}$ to obtain $T_m^{i,j}$. Box 710 may compute a variation parameter for $T_1^{i,j}$ values to obtain $STD_1$. Box 712 may compute a variation parameter for $T_k^{i,j}$ values to obtain $STD_k$. Box 714 may compute a variation parameter for $T_M^{i,j}$ values to obtain $STD_M$. Box 716 may provide Min($STD_{k'}$, for k'=1, ..., M)=$STD_k$. Box 718 may provide that pipe set k is defected. Overall thickness estimation=weighted average of $T_k^{i,j}$ for i=1, ..., $N_r$, j=1, ..., $N_f$.

The rest of the process may be similar to technique for detection of multiple defected pipes discussed above in which measurements at multiple receivers $RX_1$ to $RX_{Nr}$ and/or at multiple frequencies $f_1$ to $f_{Nf}$ are employed and for the measurement of each receiver $RX_i$ at each frequency $f_j$, that may be referred to as "channel." The corresponding estimation lines $L_1^{i,j}$ to $L_M^{i,j}$ (for producing them, each time it is assumed that the defect is on n pipes out of $N_p$ pipes with thickness change distribution profile one out of $N_t^n$ cases) may be used to provide the overall thickness estimations $T_1^{i,j}$ to $T_M^{i,j}$. Thus, the number of overall thickness estimations is $N_r N_f M$. To detect the defected pipes, it may be assumed, for example, the m-th set of pipes are actually defected (m can be any number between 1 to M), the overall thickness estimations $T_m^{i,j}$ for i=1, ..., $N_r$ and j=1, ..., $N_f$ have the least variations (are the most consistent results) while the other overall thickness estimations based on the assumption that any other set of pipes m' is defected ($T_{m'}^{i,j}$ for i=1, ..., $N_r$ and j=1, ..., $N_f$) have larger variations. Thus, when comparing the variation of the results with a suitable parameter such as standard deviation, when pipe set m is defected, the lowest standard deviation may be obtained for $T_m^{i,j}$ (for i=1, ..., $N_r$ and j=1, ..., $N_f$) estimations while for any other assumption, $T_{m'}^{i,j}$ (for i=1, ..., $N_r$, j=1, ..., $N_f$ and m'≠m) the standard deviations may be larger. This may lead to the detection of pipe set m as the defected pipes and the average or weighted average of $T_m^{i,j}$ for i=1, ..., $N_r$ and j=1, ..., $N_f$, as the most accurate overall thickness estimation result.

Detection of Class of Defected Pipes.

Although a general approach by which an arbitrary number of defected pipes can be detected was presented above, the signal to noise ratio in phase measurements may not be high enough to differentiate between the adjacent pipes in a multiple pipe inspection scenario. In other words, the accuracy of the phase measurements may not be sufficient to allow using the slight difference between the estimation lines for adjacent pipes and distinguish which one of them is defected.

Here, a more general technique is disclosed in which the pipes 300, 302, 304 and 306 (shown in FIG. 3) may be classified into groups, starting from inner-most pipes toward outer-most pipes. Each group may include a number of adjacent pipes. In this approach, the group of defected pipes may be estimated, not each individual pipe. In addition to the detection of the group of defected pipes, an accurate estimation of the overall thickness of the pipes 300, 302, 304 and 306 may be provided.

It may be assumed that in a multiple pipe configuration (pipes 1 to N), the number and which pipes are defected are unknowns. To solve this problem, the pipes 300, 302, 304 and 306 may be classified into M groups as described above for example: pipes 1 to $n_1$ are in group 1, pipes $n_{1+1}$ to $n_2$ are in group 2, and so on. Then, several RFEC estimation lines may be constructed with the number of estimation lines being equal to the number of groups M. For constructing each estimation line, the thicknesses of the pipes in the corresponding group may be changed. The rest of the process may be similar to technique directed to detection of multiple defected pipes described above in which measurements at multiple receivers $RX_1$ to $RX_{N_r}$ and/or at multiple frequencies $f_1$ to $f_{N_f}$ are employed and for the measurement of each receiver $RX_i$ at each frequency $f_j$, the corresponding estimation lines $L_1^{i,j}$ to $L_M^{i,j}$ (for producing them, each time it is assumed that the defect is on n pipes out of $N_p$ pipes) may be used to provide the overall thickness estimations $T_1^{i,j}$ to $T_M^{i,j}$. Thus, the number of overall thickness estimations is $N_r N_f M$. To detect the group of defected pipes, it may be assumed, for example, the m-th group of pipes are actually defected (m can be any number between 1 to M), the overall thickness estimations $T_m^{i,j}$ for i=1, . . . , $N_r$ and j=1, . . . , $N_f$ have the least variations (are the most consistent results) while the other overall thickness estimations based on the assumption that any other group of pipes m' is defected ($T_{m'}^{i,j}$ for i=1, . . . , $N_r$ and j=1, . . . , $N_f$) have more variation and inconsistency. Thus, when comparing the consistency of the results with a suitable parameter such as standard deviation, when pipe group m is defected, the lowest standard deviation may be obtained for $T_m^{i,j}$ (for i=1, . . . , $N_r$ and j=1, . . . , $N_f$) estimations while for any other assumption, $T_{m'}^{i,j}$ (for i=1, . . . , $N_r$, j=1, . . . , $N_f$ and m'≠m), the standard deviations may be larger. This may lead to the detection of pipe group m as the defected pipes and the average or weighted average of $T_m^{i,j}$, for i=1, . . . , $N_r$ and j=1, . . . , $N_f$, as the most accurate overall thickness estimation result.

Accordingly, methods are provided for detection of pipe characteristics, such as defect detection of downhole tubulars and overall thickness estimation of downhole tubulars, utilizing remote-field eddy current ("RFEC") technique. The methods may also be implemented with an information handing system. The systems and methods may include any of the various features of the systems and methods disclosed herein, including one or more of the following statements.

Statement 1: A defect detection method comprising: disposing a defect detection tool in a wellbore, wherein the defect detection tool comprises a transmitter and a plurality of receivers; recording measurements for a plurality of channels, wherein each channel corresponds to a particular frequency and a particular receiver; utilizing pre-calculated estimation curves corresponding to the plurality of channels at a plurality of defected candidates to obtain thicknesses corresponding to the plurality of channels at each defected candidate; and evaluating variations for the thicknesses by computing standard deviations between the thicknesses obtained for the plurality of channels at each defected candidate; utilizing a minimum variation, wherein the minimum variation comprises a minimum standard deviation to determine the plurality of defected candidates; and computing an overall thickness change using overall thickness estimations for the plurality of defected candidates.

Statement 2: The defect detection method of claim 1, wherein the computing an overall thickness change comprises calculating a weighted average of the overall thickness change estimations for the defected candidates with measurements taken from at least two receivers or at least two frequencies.

Statement 3: The defect detection method of Statement 1 or Statement 2, wherein the range for the different frequencies is from about 0.5 Hz to about 10 Hz.

Statement 4: The defect detection method of any preceding statement, wherein the estimation curves are based on maximum and minimum overall thicknesses of the plurality of defected candidates.

Statement 5: The defect detection method of any preceding statement, wherein at least two receivers and the transmitter comprise coils.

Statement 6: The defect detection method of Statement 5, wherein the coils comprise about 100 turns to about 50,000 turns.

Statement 7: The defect detection method of Statement 5, wherein a length of the coils ranges from about 1 inch to 20 inches.

Statement 8: The defect detection method of any preceding statement, wherein a spacing between at least two receivers and the transmitter ranges from about 5 inches to 80 inches.

Statement 9: The defect detection method of any preceding statement, wherein the estimation curves are based on differential phases.

Statement 10: The defect detection method of any preceding statement, wherein the smallest standard deviation is utilized as a quality factor.

Statement 11: A defect detection method comprising: disposing a pipe defect detection tool in a wellbore, wherein the pipe defect detection tool comprises a transmitter and a plurality of receivers; classifying a set of candidates into groups; recording measurements for a plurality of channels; utilizing estimation lines to obtain thicknesses of the groups; computing variations for the thicknesses to obtain standard deviations; and utilizing a minimum standard deviation to determine a defected group.

Statement 12: The defect detection method of Statement 11, wherein a number of the estimation lines are equal to a number of the groups.

Statement 13: The defect detection method of Statement 11 or Statement 12, wherein the classifying comprises grouping inner-most pipes to outer-most pipes.

Statement 14: The defect detection method of any one of Statements 11 to 13, wherein the range for the different frequencies is from about 0.5 Hz to about 2 Hz.

Statement 15: The defect detection method of any one of Statements 11 to 14, wherein the estimation lines are based on maximum and minimum overall thicknesses of the groups.

Statement 16: The defect detection method of any one of Statements 11 to 15, wherein at least two receivers and transmitter comprise coils.

Statement 17: The defect detection method of Statement 16, wherein the coils comprise about 100 to about 50,000 turns.

Statement 18: The defect detection method of Statement 16, wherein a length of the coils ranges from about 1 inch to about 20 inches.

Statement 19: The defect detection method of any one of Statements 11 to 18, wherein a spacing between at least two receivers and the transmitter ranges from about 5 inches to about 80 inches.

Statement 20: The defect detection method of any one of Statements 11 to 19, wherein the smallest standard deviation is utilized as a quality factor.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A defect detection method comprising:
   disposing a defect detection tool in a wellbore, wherein the defect detection tool comprises a transmitter and a plurality of receivers;
   recording measurements for a plurality of channels, wherein each channel corresponds to a particular frequency and a particular receiver;
   utilizing pre-calculated estimation curves corresponding to the plurality of channels at a plurality of defected candidates to obtain thicknesses corresponding to the plurality of channels at each defected candidate; and
   evaluating variations for the thicknesses by computing standard deviations between the thicknesses obtained for the plurality of channels at each defected candidate;
   utilizing a minimum variation, wherein the minimum variation comprises a minimum standard deviation to determine the plurality of defected candidates; and
   computing an overall thickness change using overall thickness estimations for the plurality of defected candidates.

2. The defect detection method of claim 1, wherein the computing an overall thickness change comprises calculating a weighted average of the overall thickness change estimations for the defected candidates with measurements taken from at least two receivers or at least two frequencies.

3. The defect detection method of claim 2, wherein the range for the different frequencies is from about 0.5 Hz to about 10 Hz.

4. The defect detection method of claim 1, wherein the estimation curves are based on maximum and minimum overall thicknesses of the plurality of defected candidates.

5. The defect detection method of claim 1, wherein at least two receivers and the transmitter comprise coils.

6. The defect detection method of claim 5, wherein the coils comprise about 100 turns to about 50,000 turns.

7. The defect detection method of claim 5, wherein a length of the coils ranges from about 1 inch to 20 inches.

8. The defect detection method of claim 1, wherein a spacing between at least two receivers and the transmitter ranges from about 5 inches to 80 inches.

9. The defect detection method of claim 1, wherein the estimation curves are based on differential phases.

10. The defect detection method of claim 1, wherein the smallest standard deviation is utilized as a quality factor.

11. A defect detection method comprising:
    disposing a pipe defect detection tool in a wellbore, wherein the pipe defect detection tool comprises a transmitter and a plurality of receivers;
    classifying a set of candidates into groups;
    recording measurements for a plurality of channels;
    utilizing estimation lines to obtain thicknesses of the groups;
    computing variations for the thicknesses to obtain standard deviations; and
    utilizing a minimum standard deviation to determine a defected group.

12. The defect detection method of claim 11, wherein a number of the estimation lines are equal to a number of the groups.

13. The defect detection method of claim 11, wherein the classifying comprises grouping inner-most pipes to outer-most pipes.

14. The defect detection method of claim 11, wherein the range for the different frequencies is from about 0.5 Hz to about 2 Hz.

15. The defect detection method of claim 11, wherein the estimation lines are based on maximum and minimum overall thicknesses of the groups.

16. The defect detection method of claim 11, wherein at least two receivers and transmitter comprise coils.

17. The defect detection method of claim 16, wherein the coils comprise about 100 to about 50,000 turns.

18. The defect detection method of claim 16, wherein a length of the coils ranges from about 1 inch to about 20 inches.

19. The defect detection method of claim 11, wherein a spacing between at least two receivers and the transmitter ranges from about 5 inches to about 80 inches.

20. The defect detection method of claim 11, wherein the smallest standard deviation is utilized as a quality factor.

\* \* \* \* \*